United States Patent [19]

Murayama et al.

[11] 3,984,371

[45] Oct. 5, 1976

[54] STABILIZATION OF SYNTHETIC POLYMERS

[75] Inventors: Keisuke Murayama; Syoji Morimura; Takao Yoshioka; Tomoyuki Kurumada, all of Tokyo, Japan

[73] Assignee: Sankyo Company Limited, Tokyo, Japan

[22] Filed: Oct. 3, 1973

[21] Appl. No.: 402,885

[30] Foreign Application Priority Data

Oct. 20, 1972 Japan............................ 47-104907

[52] U.S. Cl.................. 260/45.75 C; 260/45.75 W; 260/45.75 Q; 260/45.75 F; 260/45.8 N; 260/77.5 SS

[51] Int. Cl.²........................ C08K 5/34; C08K 5/54

[58] Field of Search.............. 260/45.75 C, 45.75 Q, 260/45.75 T, 45.8 N, 45.75 F, 45.75 W

[56] References Cited
UNITED STATES PATENTS

| | | | |
|---|---|---|---|
| 2,778,825 | 1/1957 | Melamed............................ | 260/244 |
| 3,436,369 | 4/1969 | Kitaoka et al...................... | 260/45.8 |
| 3,497,512 | 2/1970 | Hofer et al......................... | 260/250 |
| 3,573,216 | 3/1971 | Strobel et al....................... | 252/300 |
| 3,640,928 | 2/1972 | Murayama et al.................. | 260/23 |
| 3,705,166 | 12/1972 | Murayama et al............. | 260/293.86 |
| 3,759,926 | 9/1973 | Chalmers et al................. | 260/293.9 |
| 3,790,525 | 2/1974 | Murayama et al................. | 260/45.8 |
| 3,850,877 | 11/1974 | Cook .................................. | 260/45.8 |

*Primary Examiner*—Donald E. Czaja
*Assistant Examiner*—R. A. White
*Attorney, Agent, or Firm*—Toren, McGeady and Stanger

[57] ABSTRACT

A new piperidine derivative and a synthetic polymer composition stabilized against photo- and thermal deterioration thereof wherein there is incorporated, in a sufficient amount to prevent such deterioration, said piperidine derivative.

9 Claims, No Drawings

STABILIZATION OF SYNTHETIC POLYMERS

DETAILED EXPLANATION OF THE INVENTION

This invention relates to a new piperidine derivative and a synthetic polymer composition which comprises the same.

More particularly, the piperidine derivatives of this invention have the following formula

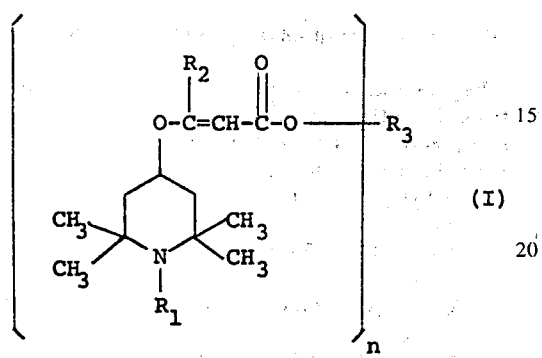

In the above formula, $R_1$ represents hydrogen atom, an alkyl group, a substituted alkyl group, an alkenyl group, an alkynyl group, an aralkyl group, an aliphatic acyl group, an alkoxycarbonyl group or an aralkoxycarbonyl group. $R_2$ represents hydrogen atom, a lower alkyl group or phenyl group. $n$ Represents an integer of 1 – 4. $R_3$ represents, when $n$ is 1, hydrogen atom, an alkyl group, a substituted or unsubstituted aralkyl group, a cycloalkyl group, an alkenyl group, an alkynyl group, an epoxyalkyl group, an aryl group or a group

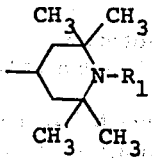

($R_1$ is as defined above), when $n$ is 2, an alkylene group, an alkenylene group, an alkynylene group, an aralkylene group, a group

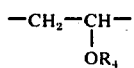

($R_4$ is an acyl group) or a divalent metal atom, when $n$ is 3, an alkanetriyl group, an aralkanetriyl group or a trivalent metal atom, and, when $n$ is 4, an alkanetetrayl group, an aralkanetetrayl group or a tetravalent metal atom.

The inventors of this invention have found that the new piperidine derivatives having the above-shown formula (I) have a stabilizing effect on synthetic polymeric materials, in particular, a property for effectively preventing photo- and thermal-deteriorations.

The term "polymeric materials" as used herein are intended to embrace, polyolefins including low- and high-density polyethylene, polypropylene, polystyrene, polybutadiene, polyisoprene, other olefin homopolymer, ethylene-propylene copolymer, ethylene-butene copolymer, ethylene-vinyl acetate copolymer, styrene-butadiene copolymer, acrylonitrile-styrene-butadiene copolymer, and other copolymers of other ethylene-forming unsaturated monomer with olefin;

polyvinyl chloride and polyvinylidene chloride including homopolymers of vinyl chloride, homopolymers of vinylidene chloride, copolymers of vinyl chloride with vinylidene chloride, copolymers of each of vinyl chloride and vinylidene chloride with vinyl acetate or other ethylene-forming unsaturated monomer;

polyacetal, for example, polyoxymethylene and polyoxyethylene;

polyester, for example, polyethylene terephthalate;

polyamide, for example, 6-nylon, 6,6-nylon and 6,10-nylon; and, polyurethane.

The synthetic polymeric materials are widely utilized in the form of various shapes, e.g., fibres, films, sheets, other molded products, latex and foams, because of their excellent properties.

The alkyl group of the $R_1$ in the above-mentioned formula (I) has carbon atoms of 1 – 8 and is, for example, methyl, ethyl, propyl, butyl or octyl; the substituted alkyl group has carbon atoms of 1 – 3 in its alkyl and is, for example, hydroxyalkyl, e.g., 2-hydroxyethyl, an alkoxyalkyl having carbon atoms of 1 – 4 in its alkoxy, e.g., 2-ethoxyethyl or ethoxymethyl, an acyloxyalkyl having aliphatic carbon atoms of 2 – 8 or aromatic carbon atoms of 7 – 11 in its acyl, e.g., 2-acetoxyethyl, 2-stearoyloxyethyl, 2-benzoyloxyethyl or 2-acrloyloxyethyl, an epoxyalkyl, e.g., 2,3-epoxypropyl, a cyanoalkyl, e.g., cyanomethyl or 2-cyanoethyl, a halogenoalkyl, e.g., 2-chloroethyl, an alkoxycarbonylalkyl having carbon atoms of 1 – 4 in its alkoxy, e.g., ethoxycarbonylmethyl, butoxycarbonylmethyl or 2-methoxycarbonylethyl; the alkenyl group has carbon atoms of 3 – 4 and is, for example, allyl; the alkynyl group has carbon atoms of 3 – 4 and is, for example, 2-propynyl; the aralkyl group has carbon atoms of 7 – 8 and is, for example, benzyl; the aliphatic acyl group has carbon atoms of 2 – 8 and is, for example, acetyl, propionyl, butyryl, octanoyl, acryloyl, methacryloyl or crotonoyl; the alkoxycarbonyl group has carbon atoms of 2 – 10 and is, for example, ethoxycarbonyl or octoxycarbonyl, and the aralkoxycarbonyl group has carbon atoms of 8 – 10 and is, for example, benzyloxycarbonyl. The particularly preferable $R_1$ is hydrogen atom, methyl group, an allyl group, benzyl group or an aliphatic acyl group having carbon atoms of 2 – 8. The lower alkyl group of the $R_2$ has carbon atoms of 1 – 4 and is, for example, methyl. The alkyl group, alkenyl group, alkynyl group and epoxyalkyl group of the $R_3$ are the same as illustrated with regard to the $R_1$. The substituted or unsubstituted aralkyl group has carbon atoms of 7 – 8 in its aralkyl wherein its phenyl may be substituted with an alkyl group having carbon atoms of 1 – 4 or hydroxy group, and is, for example, benzyl or 3,5-di-t-butyl-4-hydroxybenzyl; the cycloalkyl group has carbon atoms of 5 – 6 and is, for example, cyclohexyl; the aryl group has carbon atoms of 6 – 11 and is, for example, phenyl or tolyl; the alkylene group has carbon atoms of 2 – 6 and is, for example, ethylene, propylene, tetramethylene or hexamethylene; the alkenylene group has carbon atoms of 4 – 6 and is, for example, 2-butenylene; the alkynylene group has carbon atoms of 4 – 6 and is, for example 2-butynylene; the aralkylene group has carbon atoms of 8 – 10 and is, for example, xylylene; the group

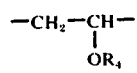

wherein $R_4$ is an aliphatic acyl group having carbon atoms of 2 – 8 is, for example,

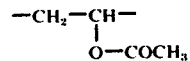

the divalent metal atom is, for example, calcium, magnesium, zinc, copper or barium; the alkanetriyl group has carbon atoms of 3 – 6 and is, for example, $-CH_2-CH-CH_2$,

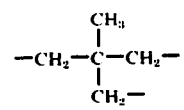

or

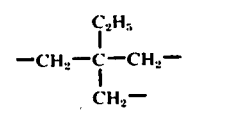

the aralkanetriyl group has carbon atoms of 9 and is, for example,

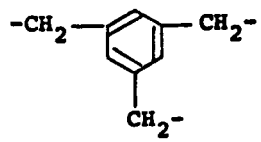

or

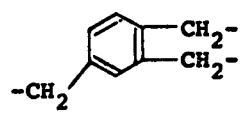

the trivalent metal atom is, for example, boron or aluminum; the alkanetetrayl group has carbon atoms of 5 and is, for example,

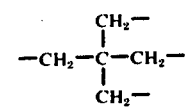

the aralkanetetrayl group has carbon atoms of 10 and is, for example

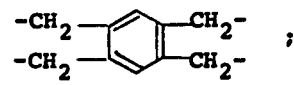

and the tetravalent metal atom is, for example, tin, silicon or titanium. The particularly preferable $R_3$ is hydrogen atom, an alkyl group having carbon atoms of 1 – 4, or the group

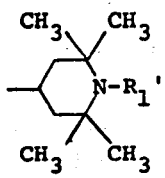

($R_1'$ is hydrogen atom or methyl group) Preferably, $n$ is 1.

Representative compounds of the piperidine derivatives (I) of this invention are illustrated below, but the compounds illustrated hereunder are not intended to limit this invention.

1. Ethyl β-(2,2,6,6-tetramethyl-4-piperidyloxy)acrylate
2. Ethyl β-(1,2,2,6,6-pentamethyl-4-piperidyloxy)acrylate
3. Methyl β-(2,2,6,6-tetramethyl-4-piperidyloxy)crotonate
4. Methyl β-(1,2,2,6,6-pentamethyl-4-piperidyloxy)-crotonate
5. Octyl β-(1,2,2,6,6-pentamethyl-4-piperidyloxy)-crotonate
6. Allyl β-(1,2,2,6,6-pentamethyl-4-piperidyloxy)-crotonate
7. 2-Propynyl β-(1,2,2,6,6-pentamethyl-4-piperidyloxy)-crotonate
8. 2,3-Epoxypropyl β-(1,2,2,6,6-pentamethyl-4-piperidyloxy)crotonate
9. 3,5-di-t-Butyl-4-hydroxybenzyl β-(1,2,2,6,6-pentamethyl-4-piperidyloxy)crotonate
10. Benzyl β-(1,2,2,6,6-pentamethyl-4-piperidyloxy)crotonate
11. Cyclohexyl β-(1,2,2,6,6-pentamethyl-4-piperidyloxy)-crotonate
12. Phenyl β-(1,2,2,6,6-pentamethyl-4-piperidyloxy)crotonate
13. 2,2,6,6-Tetramethyl-4-piperidyl β-(2,2,6,6-tetramethyl-4-piperidyloxy)crotonate
14. 1,2,2,6,6-Pentamethyl-4-piperidyl β-(1,2,2,6,6-pentamethyl-4-piperidyloxy)crotonate
15. Methyl β-(2,2,6,6,-tetramethyl-1-octyl-4-piperidyloxy)-crotonate
16. Methyl β-(1-allyl-2,2,6,6-tetramethyl-4-piperidyloxy)-crotonate
17. Methyl β-[1-(2-propynyl)-2,2,6,6-tetramethyl-4-piperidyloxy]crotonate
18. Methyl β-(1-benzyl-2,2,6,6-tetramethyl-4-piperidyloxy)-crotonate
19. Methyl β-[1-(2,3-epoxypropyl)-2,2,6,6-tetramethyl-4-piperidyloxy]crotonate
20. Methyl β-[1-(2-hydroxyethyl)-2,2,6,6-tetramethyl-4-piperidyloxy]crotonate
21. Methyl β-[1-(2-acetoxyethyl)-2,2,6,6-tetramethyl-4-piperidyloxy]crotonate
22. Methyl β-(1-ethoxycarbonylmethyl-2,2,6,6-tetramethyl-4-piperidyloxy)crotonate
23. Methyl β-(1-ethoxymethyl-2,2,6,6-tetramethyl-4-piperidyloxy)crotonate
24. Methyl β-(1-acryloyl-2,2,6,6-tetramethyl-4-piperidyloxy)-crotonate
25. Methyl β-(1-acetyl-2,2,6,6-tetramethyl-4-piperidyloxy)-crotonate 26. Methyl β-(1-ethoxycarbonyl-2,2,6,6-tetramethyl-4-piperidyloxy)crotonate
27. Methyl β-(1-benzyloxycarbonyl-2,2,6,6-tetramethyl-4-piperidyloxy)crotonate
28. Methyl β-(1-cyanomethyl-2,2,6,6-tetramethyl-4-piperidyloxy)crotonate
29. Methyl β-(1,2,2,6,6-pentamethyl-4-piperidyloxy)cinnamate
    Ethylene 1,2-bis[β-(1,2,2,6,6-pentamethyl-4-piperidyloxy)acrylate]
31. Ethylene 1,2-bis [β-(1,2,2,6,6-pentamethyl-4-piperidyloxy)crotonate]
32. 2-Butenylene 1,4-bis[β-(1,2,2,6,6-pentamethyl-4-piperidyloxy)crotonate]
33. 2-Butynylene 1,4-bis[β-(1,2,2,6,6-pentamethyl-4-piperidyloxy)crotonate]
34. p-Xylylene α,α'-bis[β-(1,2,2,6,6-pentamethyl-4-piperidyloxy)crotonate]
35. Calcium bis[β-(1,2,2,6,6-pentamethyl-4-piperidyloxy)-crotonate]
36. 3-Acetoxypropylene 1,2-bis[β-(1,2,2,6,6-pentamethyl-4-piperidyloxy)crotonate]
37. Tris [β-(1,2,2,6,6-pentamethyl-4-piperidyloxy)-crotonin]
38. 1,1,1-Tris[β-(1,2,2,6,6-pentamethyl-4-piperidyloxy)-crotonoyloxymethyl]ethane
39. 1,1,1-Tris[β-(1,2,2,6,6-pentamethyl-4-piperidyloxy)-crotonoyloxymethyl]propane
40. 1,3,5-Tris[β-(1,2,2,6,6-pentamethyl-4-piperidyloxy)-crotonoyloxymethyl]benzene
41. Boron tris [β-(1,2,2,6,6-pentamethyl-4-piperidyloxy)-crotonate]
42. Tetrakis [β-(1,2,2,6,6-pentamethyl-4-piperidyloxy)-crotonoyloxymethyl]
43. 1,2,4,5-Tetrakis [β-(1,2,2,6,6-pentamethyl-4-piperidyloxy)crotonoyloxymethyl]benzene
44. Tin tetrakis [β-(1,2,2,6,6-pentamethyl-4-piperidyloxy)-crotonate]

The piperidine derivatives (I) of this invention can be easily prepared by reacting the compounds (II) with the compounds (III) in the presence of a basic catalyst such as sodium methylate, sodium ethylate, potassium butylate or sodium hydroxide in an organic solvent such as toluene or xylene as shown in the following reaction equation:

In the above formulae, $R_1$, $R_2$, $R_3$ and $n$ are as defined above.

In this invention, the piperidine derivatives (I) employed as a stabilizer may be easily incorporated into a synthetic polymeric material by various methods commonly used in the art. The stabilizer may be added to a synthetic polymer material at any stage in the manufacture of a molded product therefrom. For example, the stabilizer of a dry powder may be admixed with a synthetic polymeric material or a suspension or emulsion of the stabilizer may be admixed therewith.

The amount of the piperidine derivative (I) which may be added to a synthetic polymeric material according to this invention is varied upon the kind, nature and purpose for use of the synthetic polymeric material to be added. In general, the amount ranging 0.01 – 5.0% by weight may be employed to the weight of a synthetic polymeric material, but a practical range may be varied upon the synthetic polymeric material and there may be used 0.01 – 2.0% by weight, preferably 0.02 – 1.0% by weight for polyolefin; 0.01 – 1.0% by weight, preferably 0.02 – 0.5% by weight for polyvinyl chloride and polyvinylidene chloride; 0.01 – 5.0% by weight, preferably 0.02 – 2.0% by weight for polyurethane and polyamide.

The above-mentioned stabilizer may be used alone or in admixture with other known antioxidants, ultraviolet absorbents, fillers, pigments and the like. Examples of such additives are illustratively shown below.

ANTIOXIDANTS

Simple 2,6-dialkylphenols,
such as, for example, 2,6-di-tert.butyl-4-methylphenol, 2-tert.butyl-4,6-dimethylphenol, 2,6-di-tert.butyl-4-methoxymethylphenol and 2,6-dioctadecyl-4-methylphenol.

Derivatives of alkylated hydroquinones,
such as, for example, 2,5-di-tert.butyl-hydroquinone, 2,5-di-tert.amyl-hydroquinone, 2,6-di-tert.butyl-hydroquinone, 2,5-di-tert.butyl-4-hydroxyanisole, 3,5-di-tert.butyl-4-hydroxyanisole and tris(3,5-di-tert.-4-

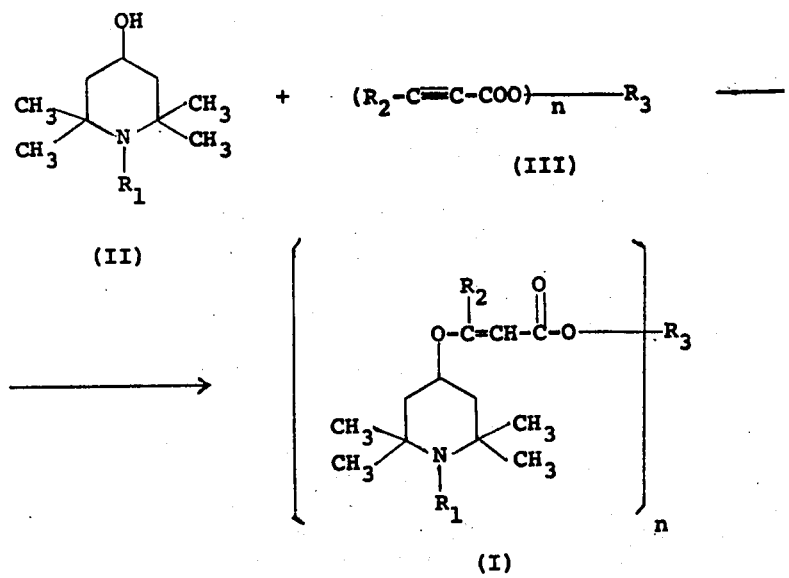

hydroxyphenyl)phosphite, 3,5-di-tert.butyl-4-hydroxyphenylstearate, di-(3,5-di-tert.butyl-4-hydroxyphenyl)adipate.

Hydroxylated thiodiphenyl ethers, such as, for example, 2,2'-thiobis(6-tert.butyl-4-methylphenol), 2,2'-thiobis-(4-octylphenol), 4,4'-thiobis(6-tert.butyl-3-methylphenol), 4,4'-thiobis(3,6-di-sec.amylphenol) and 4,4'-thiobis(6-tert.butyl-2-methylphenol), 4,4'-bis(2,6-dimethyl-4-hydroxyphenyl)disulfide.

Alkylidene-bisphenols, such as, for example, 2,2'-methylene-bis(6-tert.butyl-4-methylphenol), 2,2'-methylene-bis(6-tert.butyl-4-ethylphenol), 4,4'-methylene-bis(6-tert.butyl-2-methylphenol), 4,4-methylene-bis-(2,6-di-tert.butylphenol), 2,6-di-(3-tert.butyl-5-methyl-2-hydroxybenzyl-4-methylphenol, 2,2'-methylene-bis[4-methyl-6-(α-methylcyclohexyl)-phenol], 1,1-bis(3,5-dimethyl-2-hydroxyphenyl)-butane, 1,1-bis(5-tert.butyl-4-hydroxy-2-methylphenyl)-butane, 2,2-bis-(5-tert.butyl-4-hydroxy-2-methylphenyl)butane, 2,2-bis(3,5-di-tert.butyl-4-hydroxyphenyl)propane, 1,1,3-tris-(5-tert.butyl-4-hydroxy-2-methylphenyl)butane, 2,2-bis(5-tert.butyl-4-hydroxy-2-methylphenyl)-4-n-dodecylmercaptobutane, 1,1,5,5-tetra(5-tert.butyl-4-hydroxy-2-methylphenyl)pentane and ethylene glycol bis[3,3-bis(3'-tert.butyl-4-hydroxyphenyl)butyrate].

O-, N- and S-benzyl compounds, such as, for example, 3,5,3',5'-tetra-tert.butyl-4,4'-dihydroxydibenzylether, 4-hydroxy-3,5-dimethylbenzyl-mercaptoacetic acid octadecyl ester, tri(3,5-di-tert.butyl-4-hydroxybenzyl)amine, and bis(4-tert.butyl-3-hydroxy-2,6-dimethylbenzyl)dithiolterephthalate.

Hydroxybenzylated malonic esters, such as, for example, 2,2-bis(3,5-di-tert.butyl-2-hydroxybenyl)malonic acid dioctadecyl ester, 2-(3-tert.butyl-4-hydroxy-5-methylbenzyl)malonic acid dioctadecyl ester, 2,2-bis-(3,5-di-tert.butyl-4-hydroxybenzyl)malonic acid didodecylmercaptoethyl ester and 2,2-bis(3,5-di-tert.butyl-4-hydroxybenzyl)malonic acid di(4-tert.octylphenyl)-ester.

Hydroxybenzyl-aromatics, such as, for example, 1,3,5-tri(3,5-di-tert.butyl-4-hydroxybenzyl)-2,4,6-trimethylbenzene, 1,4-di(3,5-di-tert.butyl-4-hydroxybenzyl)-2,3,5,6-tetramethylbenzene and 2,4,6-tri(3,5-di-tert.butyl-4-hydroxybenzyl)-phenol.

s-Triazine compounds, such as, for example, 2,4-bis-octylmercapto-6-(3,5-di-tert.butyl-4-hydroxyanilino)-s-triazine, 2-octylmercapto-4,6-bis(3,5-di-tert.butyl-4-hydroxyanilino)-s-triazne, 2-octylmercapto-4,6-bis-(3,5-di-tert.butyl-4-hydroxyphenoxy)-s-triazine, 2,4,6-tris(3,5-di-tert.butyl-4-hydroxyphenoxy)-s-triazine, 2,4,6-tris(3,5-di-tert.butyl-4-hydroxyphenylethyl)-s-triazine and 1,3,5-tris(3,5-di-tert.butyl-4-hydroxybenzyl)isocyanurate.

Amides of 3,5-di-tert.butyl-4-hydroxyphenylpropionic acid, such as, for example, 1,3,5-tris(3,5-di-tert.butyl-4-hydroxyphenyl-propionyl)-hexahydro-s-triazine and N,N'-bis(3,5-di-tert.butyl-4-hydroxyphenylpropionyl)-hexamethylenediamine.

Esters of 3,5-di-tert.butyl-4-hydroxyphenylpropionic acid with monohydric or polyhydric alcohols, such as, for example, methanol, ethanol, octadecanol, 1,6-hexanediol; 1,9-nonanediol, ethylene glycol, 1,2-propanediol, diethylene glycol, thiodiethylene glycol, neopentyl glycol, pentaerythritol, 3-thiaundecanol, 3-thia-pentadecanol, trimethylhexanediol, trimethylolethane, trimethylolpropane, tris-hydroxyethyl-isocyanurate and 4-hydroxymethyl-1-phospha-2,6,7-trioxabicyclo[2,2,2]octane.

Esters of 5-tert.butyl-4-hydroxy-3-methylphenylpropionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thia-pentadecanol, trimethylhexanediol, trimethylolethane, trimethylolpropane, tris-hydroxyethyl-iso-cyanurate and 4-hydroxymethyl-1-phospha-2,6,7-trioxabicyclo[2,2,2]octane.

Esters of 3,5-di-tert.butyl-4-hydroxyphenylacetic acid with monohydric or polyhydric alcohols, such as, for example, methanol, ethanol, octadecanol, 1,6-hexanediol, 1,9-nonanediol, ethylene glycol,1,2-propanediol, diethylene glycol, thiodiethylene glycol, neopentyl glycol, pentaerythritol, 3-thiaundecanol, 3-thia-pentadecanol, trimethylhexanediol, trimethylolethane, trimethylolpropane, tris-hydroxyethylisocyanurate and 4-hydroxymethyl-1-phospha-2,6,7-tri-oxa-bicyclo[2,2,2]octane.

Acylaminophenols, such as, for example,N-(3,5-di-tert.butyl-4-hydroxyphenyl)stearic acid amide and N,N'-bis(3,5-di-tert.butyl-4-hydroxyphenyl)-thio-bis-acetamide.

Benzylphosphonates, such as, for example, 3,5-di-tert.butyl-4-hydroxybenzylphosphonic acid dimethyl ester, 3,5-di-tert.butyl-4-hydroxybenzylphosphonic acid diethyl ester, 3,5-di-tert.butyl-4-hydroxybenzylphosphonic acid dioctadecyl ester and 5-tert.-butyl-4-hydroxy-3-methylbenzylphosphonic acid dioctadecyl ester.

Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydro-quinoline, mono- and di-octyliminodibenzyl and polymerised 2,2,4-trimethyl-1,2-dihydroquinoline.

UV-absorbers and light protection agents 2-(2'-Hydroxyphenyl)-benztriazoles, such as, for example, the 5'-methyl-, 3',5'-di-tert.butyl-, 5'-tert.butyl-, 5'-(1,1,3,3-tetramethyl-butyl)-, 5-chloro-3',5'-di-tert.butyl-, 5-chloro-3'-tert.butyl-5'-methyl-, 3'-sec.butyl-5'-tert.butyl-, 3'-[α-methylbenzyl]-5'-methyl-, 3'-[α-methylbenzyl]5'-methyl-5-chloro-, 4'-hydroxy-, 4'-methoxy-, 4'-octoxy-, 3',5'-di-tert.amyl-, 3'-methyl-5'-carbomethoxyethyl- or 5-chloro-3',5'-di-tert.amyl-derivatives.

2,4-Bis(2'-hydroxyphenyl)-5-alkyl-s-triazines, such as, for example, the 6-ethyl-, 6-undecyl- or 6-heptadecyl-derivatives.

2-Hydroxy-benzophenones, such as, for example, the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivatives.

1,3-Bis(2'-hydroxy-benzoyl)benzenes, such as, for example, 1,3-bis(2'-hydroxy-4'-hexyloxy-benzoyl)-benzene, 1,3-bis(2'-hydroxy-4'-octoxybenzoyl)benzene and 1,3-bis(2'-hydroxy-4'-dodecyloxy-benzoyl)benzene.

Esters of optionally substituted benzoic acids, such as, for example, phenyl salicylate, octylphenyl salicylate, di-benzoylresorcinol, bis(4-tert.butylbenzoyl)resorcinol, benzoyl-resorcinol, 3,5-di-tert.butyl-4-hydroxybenzoic acid 2,4-di-tert.butylphenyl ester, octadecyl ester or 2-methyl-4,6-di-tert.butylphenyl ester.

Acrylates, such as, for example, α-cyano-β,β-diphenylacrylic acid ethyl ester or isooctyl ester, α-carbomethoxycinnamic acid methyl ester, α-cyano-β-methyl-p-methoxycinnamic acid methyl ester or butyl ester and N-(β-carbomethoxy-vinyl)-2-methylindoline.

Nickel compounds, such as, for example, nickel complexes of 2,2'-thiobis(4-tert.octylphenol), such as the 1:1 and 1:2 complex, optionally with other ligands such as n-butylamine, triethanolamine or N-cyclohexyl-diethanolamine, nickel complexes of bis(4-tert.octylphenyl)-sulphone, such as the 2:1 complex, optionally with other ligands such as 2-ethyl-caproic acid, nickel dibutyldithiocarbamate, nickel salts of 4-hydroxy-3,5-di-tert.butylbenzylphosphonic acid monoakyl esters, such as the methyl, ethyl or butyl ester, the nickel complex of 2-hydroxy-4-methyl-phenyl-undecyl-ketonoxime and nickel 3,5-di-tert.butyl-4-hydroxybenzoate.

Oxalic acid diamides, such as, for example, 4,4'-di-octyloxyanilide, 2,2'-dioctyloxy-5,5'-di-tert.-butyloxanilide, 2,2'-didodecyloxy-5,5'-di-tert.butyloxanilide, 2-ethoxy-5-tert.butyl-2'-ethyloxanilide, 2-ethoxy-2'-ethyl-oxanilide, N,N'-bis(3-dimethylaminopropyl)oxalamide, mixtures of o- and p-methoxy and o- and p-ethoxy-di-substituted oxanilides and mixtures of 2-ethoxy-5-tert.butyl-2'-ethyloxanilide with 2-ethoxy-2'-5,4'-di-tert.butyloxanilide.

Metal deactivators, such as, for example, oxanilide, isophthalic acid dihydrazide, sebacic acid bis-phenylhydrazide, bis-benzylidene oxalic acid di-hydrazide, N,N'-diacetyl-adipic acid dihydrazide, N,N'-bis-salicyloyl-oxalic acid dihydrazide, N,N'-bis-salicyloylhydrazine and N,N'-bis-(3,5-di-tert.butyl-4-hydroxyphenyl-propionyl)hydrazine.

Phosphites, such as, for example triphenylphosphite, di-phenyl alkyl-phosphites, phenyl dialkylphosphites, trinonylphenylphosphite, trilaurylphosphite, tri-octadecylphosphite, 3,9-di-isodecyloxy-2,4,8,10-tetraoxa-3,9-diphospha-spiro[5.5]undecane and tris-(4-hydroxy-3,5-di-tert.butylphenyl)phosphite.

Compounds which destroy peroxide, such as, for example, esters of β-thiodipropionic acid, e.g., the lauryl, stearyl, myristryl or tridecyl ester, salts of 2-mercaptobenzimidazole, e.g., the zinc salt, and diphenylthiourea.

Polyamide stabilizers, such as, for example, copper salts in combination with iodides and/or phosphorus compounds and salts of divalent manganes.

Basic co-stabilizers, such as, for example, polyvinylpyrrolidone, malamine, benzoguanamine, triallyl cyanurate, dicyandiamide, urea derivatives, hydrazine derivatives, amines, polyamides, polyurethanes and alkali metal salts and alkaline earth metal salts of higher saturated or unsaturated fatty acids, e.g., Ca stearate, Mg laurate, Na ricinoleate, K palmitate and Zn stearate.

PVC stabilizers, such as, for example, organic tin compounds, organic lead compounds and Ba/Cd salts of fatty acids.

Nucleating agents, such as, for example, 4-tert.-butylbenzoic acid, adipic acid and diphenylacetic acid.

Other additives, such as, for example, plasticizers, lubricants, e.g., glycerine, monostearate, emulsifiers, antistatic agents, flameproofing agents, pigments, carbon black, asbestos, glass fibres, kaolin and talc.

Other additive such as these may be usually blended into the piperidine derivative (I) of this invention and advantageously employed at a ratio of 0.5 – 3 to 1.

Examples 1 to 8 describe the synthetic polymer compositions having incorporated therein the piperidine derivative (I) and their stabilizing effects and Referential Example describes the preparation of the piperidine derivative (I).

EXAMPLE 1

Into 100 parts of polypropylene ["Noblen JHH-G", trade name, after twice recrystallizations from monochlorobenzene, available from Mitsui Toatsu Chemicals Inc.] was incorporated 0.25 part of the stabilizer of this invention. The resulting mixture was blended and molten. The molten mixture was molded into a sheet with a thickness of 0.5 mm. under heating and pressure.

The sheet was exposed to irradiation of ultraviolet ray at 45° C in a fade-meter and the time when the sheet becomes brittle was measured.

The results are shown in Table 1. The stabilizers numbered hereinafter are referred to hereinbefore.

EXAMPLE 2

Into 100 parts of high-density polyethylene ["Hi-Zex", trade name, available from Mitsui Toatsu Chemicals Inc., after twice recrystallizations from toluene] was incorporated 0.25 part of the stabilizer of this invention. The resulting mixture was blended and molten and molded into a sheet with a thickness of 0.5 mm. under heating and pressure.

The sheet was exposed to irradiation of ultraviolet ray at 45° C in a fade-meter and the time when the sheet becomes brittle was measured.

The results are given in Table 1.

Table 1

| Stabilizer No. | Polypropylene | | High-density Polyethylene | |
|---|---|---|---|---|
| 2 | 740 | hrs. | 1580 | hrs. |
| 3 | 700 | | 1680 | |
| 4 | 780 | | 1640 | |
| 8 | 860 | | 1840 | |
| 11 | 740 | | 1420 | |
| 13 | 1060 | | 2120 | |
| 14 | 1040 | | 2020 | |
| 18 | 800 | | 1780 | |
| 19 | 920 | | 2040 | |
| 22 | 720 | | 1580 | |
| 24 | 700 | | 1460 | |
| 31 | 780 | | 1760 | |
| 35 | 960 | | 2100 | |
| None | 60 | | 400 | |

EXAMPLE 3

Into 100 parts of polystyrene ["Styron", trade name, after recrystallization from a mixture of benzene with methanol, available from Asahi-Dow Limited] was incorporated 0.25 part of the stabilizer of this invention. The resulting mixture was molded at 180° C under pressure into a plate with a thickness of 1 mm.

The plate thus formed was subjected to the exposure of ultraviolet ray irradiation in a fade meter at 45° C for 500 hours. A test piece of the treated plate was tested for color difference by means of a color-difference colorimeter according to the method prescribed in Japanese Industrial Standard (JIS) "K-7103", and a change of the yellowness index of the plate was calculated according to the following equation:

$$\Delta YI = YI - yi_o$$

wherein $\Delta YI$ means a change of yellowness index, $YI$ means a yellowness index after exposure and $YI_0$ means an initial yellowness index of a test piece.

The results are shown in Table 2.

Table 2

| Stabilizer No. | $YI_0$ | $\Delta YI$ |
|---|---|---|
| 3 | 4.3 | +3.1 |
|  |  | +2.8 |
| 13 | 4.5 | +3.3 |
| 14 | 4.2 | +4.4 |
| 19 | 4.6 | +2.9 |
| 35 | 4.4 | +17.1 |
| None | 4.3 | +17.1 |

EXAMPLE 4

Into 100 parts of ABS resin ["Kane Ace B–12", trade name, available from Kanagafuchi Chemical Industries Co., Ltd.] was incorporated 0.5 part of the stabilizer of this invention. The resulting mixture was kneaded on a kneading roll at 160° C for 6 minutes and then molded into a sheet with a thickness of about 0.5 mm.

The sheet was treated in a sunshine weather-ometer for 50 hours and tested for retentions of ultimate elongation and of ultimate tensile strength as well as coloration degree were determined by a conventional tensile test method. The results are shown in Table 3.

Table 3

| Stabilizer No. | Retention of elongation | Retention of tensile strength |
|---|---|---|
| 3 | 71 | 77 |
| 4 | 67 | 75 |
| 13 | 75 | 79 |
| 19 | 72 | 80 |
| 31 | 76 | 82 |
| None | 51 | 68 |

EXAMPLE 5

Into 100 parts of 6-nylon resin ["CM1011", trade name, available from Toray Industries Inc.] was incorporated 0.25 part of the stabilizer of this invention. The resulting mixture was heated and melted and then molded into a film having a thickness of about 0.1 mm. under pressure by a conventional compression molding machine.

The film thus formed was aged under the following aging condition and thereafter subjected to a tensile test to determine the retentions of tensile strength and elongation.

Aging conditions
1. Exposure to ultraviolet ray for 200 hours in a fade-meter at 45° C.
2. Aging at 160° C for 2 hours in a Geer's aging tester. The results are shown in Table 4.

Table 4

| | Fade-meter | | Geer's aging tester | |
|---|---|---|---|---|
| Stabilizer No. | Retention of ultimate elongation | Retention of ultimate tensile strength | Retention of ultimate elongation | Retention of ultimate tensile strength |
| 3 | 68% | 74% | 71% | 65% |
| 13 | 79 | 83 | 77 | 74 |
| 19 | 77 | 81 | 78 | 76 |
| 35 | 80 | 84 | 83 | 78 |
| None | 19 | 50 | 18 | 53 |

EXAMPLE 6

Into 100 parts of polyurethane resin prepared from polycaprolactone ["E-5080", trade name, available from The Nippon Elastollan Industries Ltd.] was incorporated 0.5 part of the stabilizer of this invention. The resulting mixture was heated and melted and then molded into a sheet having a thickness of about 0.5 mm.

The sheet thus formed was subjected to the exposure to ultraviolet ray in a fade-meter at 45° C for 15 hours and then tested for the retentions of ultimate elongation and ultimate tensile strength.

The results are shown in Table 5.

Table 5

| Stabilizer No. | Retention of ultimate elongation | Retention of ultimate tensile strength |
|---|---|---|
| 3 | 85% | 88% |
| 13 | 95 | 96 |
| 19 | 92 | 93 |
| None | 74 | 52 |

EXAMPLE 7

Into 100 parts of polyvinyl chloride resin ["Geon 103EP", trade name, available from The Nippon Zeon Co. Ltd] were incorporated 3 parts of butyl tin maleate, 0.5 part of butyl stearate and 0.25 part of the stabilizer of this invention and the resulting mixture was kneaded for 5 minutes on a kneading roll at 180° C and formed into a sheet with a thickness of 0.5 mm. The sheet was treated in a sunshine weather-ometer for 300 hours and then the discoloration thereof was observed. The resultd are shown in Table 6.

Table 6

| Stabilizer No. | Weather-ometer |
|---|---|
| 3 | Pale brown |
| 13 | " |
| 19 | Orange-yellow |
| None | Dark brown |

EXAMPLE 8

Into 100 parts of polyester resin ["Ester-G13", trade name, available from Mitsui Toatsu Chemicals, Inc.] were dissolved and mixed 1 part of benzoyl peroxide and 0.2 part of the stabilizer. The resulting mixture was cured by preheating at 60° C for 30 minutes and then heating at 100° C for addtional 1 hour to be formed into a plate with a thickness of 3 mm.

The plate thus formed was exposed to irradiation in the sunshine weather-ometer for 60 hours and the change of yellowness index thereof was determined according to the same method as described in the above Example 3.

The results are shown in Table 7.

Table 7

| Stabilizer No. | YI$_0$ | ΔYI |
|---|---|---|
| 3 | 2.0 | +7.0 |
| 13 | 2.2 | +8.6 |
| 14 | 2.4 | +7.6 |
| 19 | 2.6 | +7.7 |
| None | 1.8 | +13.1 |

REFERENTIAL EXAMPLE 1

Methyl β-(1,2,2,6,6-pentamethyl-4-piperidyloxy)-corolonate

To 6.2 g. of 4-hydroxy-1,2,2,6,6-pentamethyl-piperidine were added 4.26 g. of methyl tetrolate and 150 ml. of xylene. To the solution was added under ice-cooling 3 ml. of a methanolic solution of sodium methylate (0.39 g.). The solution was heated under reflux for 8 hours. After cooling, 200 ml. of water was added and separated. The aqueous layer was extracted with ether and the ether solution was combined with the separated xylene layer, washed with water, dried and subjected to distillation under reduced pressure to give the desired product as colorless liquids boiling at 120°– 122° C/0.1 mmHg.

Analysis for $C_{15}H_{27}NO_3$ : Calculated: C, 66.88%; H, 10.10%; N, 5.20%. Found : C, 66.59%; H, 10.36%; N, 5.00%. IR spectra (liquid film) : $\nu_{C=O}$ 1710; $\nu_{C=C}$ 1620, $\nu_{C-O}$ 1140 cm$^{-1}$.

Physical properties of the compounds prepared according to the methods as shown in the above Referential Example are as follows:

Ethyl β-(1,2,2,6,6-pentamethyl-4-piperidyloxy)-acrylate bp. 106°– 109° C/0.06 mmHg Methyl β-(2,2,6,6-tetramethyl-4-piperidyloxy)crotonate m.p. 66 – 67° C 2,2,6,6-Tetramethyl-4-piperidyl β-(2,2,6,6-tetramethyl-4-piperidyloxy)crotonate mp. 99° C 1,2,2,6,6-Pentamethyl-4-piperidyl β-(1,2,2,6,6-pentamethyl-4-piperidyloxy)crotonate mp. 136 – 137°C Methyl β-[1-(2,3-epoxypropyl)-2,2,6,6-tetramethyl-4-piperidyloxy)]crotonate mp. 81 – C Methyl β-(1-allyl-2,2,6,6-tetramethyl-4-piperidyloxy)crotonate mp. 54 – 55° C Methyl β-(1-benzyl-2,2,6,6-tetramethyl-4-piperidyloxy)crotonate mp. 115 – 116° C

What is claimed is:

1. A synthetic polymer composition stabilized against photo- and thermal deterioration thereof wherein there is incorporated, in a sufficient amount to prevent such deterioration, a compound having the formula

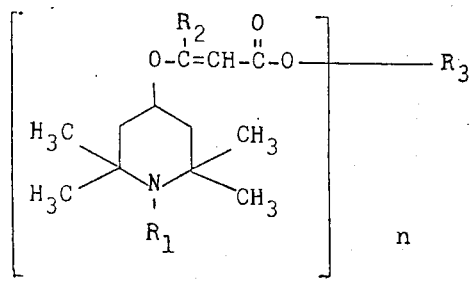

wherein
n is an integer of 1 to 4,
R$_1$ represents a hydrogen atom, an alkyl group, a hydroxyalkyl, alkoxyalkyl, aliphatic or aromatic acyloxyalkyl, epoxyalkyl, cyanoalkyl, halogenoalkyl or alkoxycarbonylalkyl group, an alkenyl group, an alkynyl group, an aralkyl group, an aliphatic acyl group, an alkoxycarbonyl group or an aralkoxycarbonyl group,
R$_2$ represents a hydrogen atom, a lower alkyl group or a phenyl group, and
R$_3$ represents, when n is 1, a hydrogen atom, an alkyl group, an aralkyl group, an aralkyl group which is substituted on its aryl by alkyl groups having 1 to 4 carbon atoms and/or by hydroxy groups, cycloalkyl group, an alkenyl group, an alkynyl group, an epoxyalkyl group, an aryl group or a group

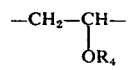

wherein R$_1$ is as defined above,
when n is 2, an alkylene group, an alkenylene group, an alkynylene group, an aralkylene group, a group $$-CH_2-\underset{\underset{OR_4}{|}}{CH}-$$

wherein R$_4$ is an acyl group, or a divalent metal atom selected from calcium, magnesium, zinc copper and barium,
when n is 3, an alkanetriyl group, an aralkanetriyl group, a trivalent metal atom selected from boron and aluminum, and
when n is 4, an alkanetetrayl group, an aralkanetetrayl group or a tetravalent metal atom selected from tin, silicon and titanium.

2. A synthetic polymer composition stabilized against photo- and thermal deterioration thereof wherein there is incorporated, in a sufficient amount to prevent such deterioration, a compound having the formula

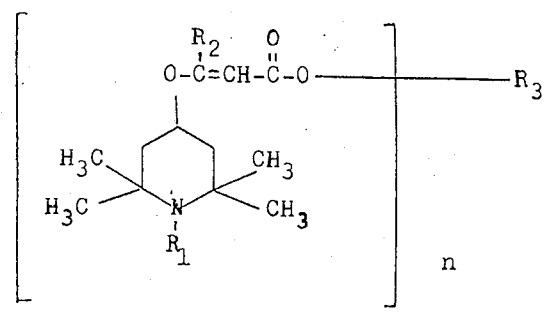

wherein
R$_1$ represents a hydrogen atom, an alkyl group having 1 to 8 carbon atoms, a substituted alkyl group having 1 to 3 carbon atom in its alkyl and which is selected from the group consisting of hydroxyalkyl, alkoxyalkyl having 1 to 4 carbon atoms in its alkoxy, aliphatic acyloxyalkyl having 2 to 18 carbon atoms in its acyl, aromatic acyloxyalkyl having 7 to 11 carbon atoms in its acyl, epoxyalkyl, cyanoalkyl, halogenoalkyl and alkoxycarbonylalkyl having 1 to 4 carbon atoms in its alkoxy; an alkenyl group having 3 or 4 carbon atoms, an alkynyl group having 3 or 4 carbon atoms, an aralkyl group having 7 or 8 carbon atoms, an aliphatic acyl group having 2 to 8 carbon atoms, an alkoxycarbonyl group having 2 to 10 carbon atoms, or an aralkoxycarbonyl group having 8 to 10 carbon atoms, $R_2$ represents a hydrogen atom, an alkyl group having 1 to 4 carbon atoms or a phenyl group, $n$ is an integer of 1 to 4, and $R_3$ represents, when $n$ is 1, a hydrogen atom, an alkyl, alkenyl, alkynyl or epoxyalkyl group as defined under $R_1$; a phenylalkyl group having 7 or 8 carbon atoms in its phenylalkyl and which may be substituted on its phenyl by hydroxy and/or alkyl groups having 1 to 4 carbon atoms, a cycloalkyl group having 5 or 6 carbon atoms, and aryl group having 6 to 11 carbon atoms or a group

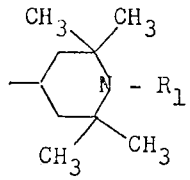

wherein $R_1$ is as defined above when $n$ is 2, an alkylene group having 2 to 6 carbon atoms, an alkenylene group having 4 to 6 carbon atoms, an alkynylene group having 4 to 6 carbon atoms, an aralkylene group having 8 to 10 carbon atoms, a group

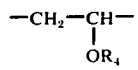

wherein $R_4$ represents an aliphatic acyl group having 2 to 8 carbon atoms, or a divalent metal atom selected from calcium, magnesium, zinc, copper and barium;

when $n$ is 3, an alkanetriyl group having 3 to 6 carbon atoms, an aralkanetriyl group having 9 carbon atoms, a trivalent metal atom selected from boron and aluminum; and when $n$ is 4, an alkanetetrayl group having 5 carbon atoms, an aralkanetetrayl group having 10 carbon atoms or a tetravalent metal atom selected from tin, silicon and titanium.

3. A synthetic polymer composition stabilized against photo- and thermal deterioration thereof wherein there is incorporated, in a sufficient amount to prevent such deterioration, a compound having the formula

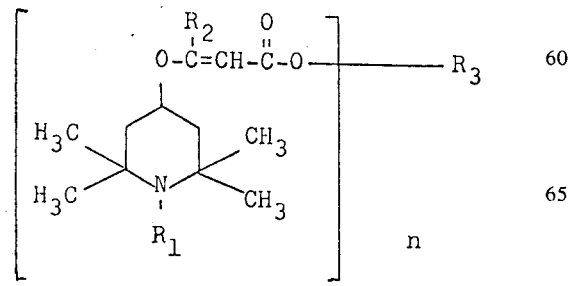

wherein $n$ is 2, 3, or 4, $R_1$ represents a hydrogen atom, an alkyl group, a hydroxyalkyl, alkoxyalkyl, aliphatic or aromatic acyloxyalkyl, epoxyalkyl, cyanoalkyl, halogenoalkyl or alkoxycarbonylalkyl group, an alkenyl group, an alkynyl group, an aralkyl group, an aliphatic acyl group, an alkoxycarbonyl group or an aralkoxycarbonyl group, $R_2$ represents a hydrogen atom, a lower alkyl group or a phenyl group, and $R_3$ represents when $n$ is 2, an alkylene group, an alkenylene group, an alkynylene group, an aralkylene group, a group

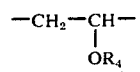

wherein $R_4$ is an acyl group, or a divalent metal atom selected from calcium, magnesium, zinc, copper and barium, when $n$ is 3, an alkanetriyl group, an aralkanetriyl group, a trivalent metal atom selected from boron and aluminum, and when $n$ is 4, an alkanetetrayl group, an aralkanetetrayl group or a tetravalent metal atom selected from tin, silicon and titanium.

4. A synthetic polymer composition stabilized against photo- and thermal deterioration thereof wherein there is incorporated, in a sufficient amount to prevent such deterioration, a compound having the formula

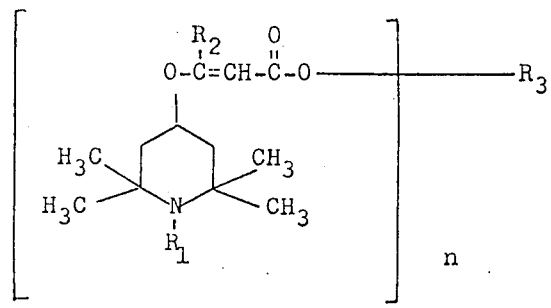

wherein $R_1$ represents a hydrogen atom, an alkyl group having 1 to 8 carbon atoms, a substituted alkyl group having 1 to 3 carbon atom in its alkyl and which is selected from the group consisting of hydroxyalkyl, alkoxyalkyl having 1 to 4 carbon atoms in its alkoxy, aliphatic acyloxyalkyl having 2 to 18 carbon atoms in its acyl, aromatic acyloxyalkyl having 7 to 11 carbon atoms in its acyl, epoxyalkyl, cyanoalkyl, halogenoalkyl and alkoxycarbonylalkyl having 1 to 4 carbon atoms in its alkoxy; an alkenyl group having 3 or 4 carbon atoms, an alkynyl group having 3 or 4 carbon atoms, an aralkyl group having 7 or 8 carbon atoms, an aliphatic acyl group having 2 to 8 carbon atoms, an alkoxycarbonyl group having 2 to 10 carbon atoms, or an aralkoxycarbonyl group having 8 to 10 carbon atoms, $R_2$ represents a hydrogen atom, an alkyl group having 1 to 4 carbon atoms or a phenyl group, $n$ is 2, 3, or 4, and $R_3$ represents when $n$ is 2, an alkylene group having 2 to 6 carbon atoms, an alkenylene group having 4 to 6 carbon atoms, an alkylene group having 4 to 6 carbon atoms, an aralkylene group having 8 to 10 carbon atoms, a group

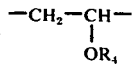

wherein $R_4$ represents an aliphatic acyl group having 2 to 8 carbon atoms, or a divalent metal atom selected from calcium, magnesium, zinc, copper and barium;

when $n$ is 3, an alkanetriyl group having 3 to 6 carbon atoms, an aralkanetriyl group having 9 carbon atoms, a trivalent metal atom selected from boron and aluminum; and when $n$ is 4, an alkanetetrayl group having 5 carbon atoms, an aralkanetetrayl group having 10 carbon atoms or a tetravalent metal atom selected from tin, silicon and titanium.

5. The synthetic polymer composition according to claim 2 wherein said polymer is a polyolefin.

6. The synthetic polymer composition according to claim 2 wherein said polymer is a polyvinyl chloride.

7. The synthetic polymer composition according to claim 2 wherein said polymer is a polyurethane.

8. The synthetic polymer composition according to claim 2 wherein said polymer is a polyamide having recurring amide groups as integral parts of the main polymer chain.

9. The synthetic polymer composition according to claim 2 wherein said polymer is a polyester.

* * * * *